United States Patent
Huang et al.

(10) Patent No.: US 9,782,444 B2
(45) Date of Patent: Oct. 10, 2017

(54) **PREPARATION AND USE OF FISH SKIN FERMENTATION LIQUID OBTAINED BY FERMENTING FISH SKIN WITH *ASPERGILLUS***

(71) Applicant: FOOD INDUSTRY RESEARCH AND DEVELOPMENT INSTITUTE, Hsinchu (TW)

(72) Inventors: Shu-Chen Huang, Hsinchu (TW); Pei-Jou Liu, Hsinchu (TW); Chiao-Ming Liao, Hsinchu (TW); Hing-Yuen Chan, Hsinchu (TW)

(73) Assignee: FOOD INDUSTRY RESEARCH AND DEVELOPMENT INSTITUTE, Hsinchu (TW)

( * ) Notice: Subject to any disclaimer, the term of this patent is extended or adjusted under 35 U.S.C. 154(b) by 0 days.

(21) Appl. No.: 15/163,005

(22) Filed: May 24, 2016

(65) Prior Publication Data

US 2016/0263165 A1   Sep. 15, 2016

Related U.S. Application Data

(60) Continuation-in-part of application No. 14/450,720, filed on Aug. 4, 2014, now abandoned, which is a division of application No. 13/240,231, filed on Sep. 22, 2011, now abandoned.

(30) Foreign Application Priority Data

Nov. 3, 2010 (TW) .................. 99137850 A

(51) Int. Cl.
    *A61K 35/60* (2006.01)
    *C12P 1/02* (2006.01)
    *C12N 9/02* (2006.01)
    *A23L 17/00* (2016.01)

(52) U.S. Cl.
    CPC .............. *A61K 35/60* (2013.01); *A23L 17/00* (2016.08); *A23L 17/65* (2016.08); *C12N 9/0071* (2013.01); *C12P 1/02* (2013.01); *C12N 2502/09* (2013.01); *C12Y 114/18001* (2013.01)

(58) Field of Classification Search
    CPC ............. C12N 1/20; A61K 8/99; A61K 35/60
    See application file for complete search history.

*Primary Examiner* — Ruth Davis
(74) *Attorney, Agent, or Firm* — WPAT, P.C., Intellectual Property Attorneys; Anthony King

(57) ABSTRACT

The present invention relates to a method for fermenting fish skin by using *Aspergillus*. Also provided is a use of the fermentation liquid obtained by fermenting fish skin with *Aspergillus* obtained from the method in inhibiting the activity of tyrosinase, inhibiting the activity of angiotensin-converting enzyme and/or improving the survival of fibroblasts.

4 Claims, No Drawings

PREPARATION AND USE OF FISH SKIN FERMENTATION LIQUID OBTAINED BY FERMENTING FISH SKIN WITH ASPERGILLUS

FIELD OF THE INVENTION

The present invention relates to a method for preparing a fish skin fermentation liquid obtained by fermenting fish skin with *Aspergillus* prepared by fermenting fish skin with *Aspergillus*. The fermentation liquid obtained by fermenting fish skin with *Aspergillus* prepared by the method of the present invention can inhibit the activity of tyrosinase, inhibit the activity of angiotensin-converting enzyme and/or improve the survival of fibroblasts.

BACKGROUND OF THE INVENTION

Taiwan is an island system with advanced aquaculture technology and large-scale fishery production. In the course of processing aquatic products, a large amount of waste is produced, including fish skin.

Fish skin is rich in collagen, and methods for obtaining collagen from fish skin or from fish scales such as that of Taiwan tilapia fish (*Tilapia*) are described in R.O.C. (Taiwan) Patent Publication Nos. 200535141, 200902039 and 201000111 and R.O.C. Patent No. 1263678. R.O.C. Patent Publication No. 200927190 discloses a hydrolyzate obtained by fermenting fish skin of monacanthidae with *Bacillus subtilis* natto; the hydrolyzate has an antioxidant effect and can be used to promote proliferation of skin fibroblasts and production of protocollagen.

However, there is room for further development in use of fish skin.

SUMMARY OF THE INVENTION

The purpose of the invention is to provide a fermentation liquid obtained by fermenting fish skin with *Aspergillus* prepared by fermenting fish skin with *Aspergillus*. The fermentation liquid obtained by fermenting fish skin with *Aspergillus* is able to inhibit the activity of tyrosinase, inhibit the activity of angiotensin-converting enzyme and/or improve the survival of fibroblasts.

One purpose of the present invention is to provide a method for preparing a fish skin fermentation liquid obtained by fermenting fish skin with *Aspergillus*, which method comprises co-culturing the fish skin and *Aspergillus* in a medium.

Another purpose of the present invention is to provide a fermentation liquid obtained by fermenting fish skin with *Aspergillus* prepared by the method mentioned above.

Another purpose of the present invention is to provide a composition, which comprises the fish skin fermentation liquid obtained by fermenting fish skin with *Aspergillus* mentioned above.

Another purpose of the present invention is to provide a use of the composition mentioned above in inhibiting the activity of tyrosinase, inhibiting the activity of angiotensin-converting enzyme and/or improving the survival of fibroblasts.

Another purpose of the present invention is to provide a method for inhibiting the activity of tyrosinase, inhibiting the activity of angiotensin-converting enzyme and/or improving the survival of fibroblasts in a subject in need of such inhibition and/or improvement, which comprises administering to said subject an effective amount of the fish skin fermentation liquid obtained by fermenting fish skin with *Aspergillus*/composition mentioned above.

Another purpose of the present invention is to provide a method for inhibiting the activity of angiotensin-converting enzyme in a subject in need of such inhibition comprising administering to said subject an effective amount of a fish skin fermentation composition obtained by co-culturing a fish skin and *Aspergillus* in a medium and collecting the supernatant.

DETAILED DESCRIPTION OF THE INVENTION

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the compounds of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±10%.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "preventing" or "prevention" is recognized in the art, and when used in relation to a condition, it includes administering, prior to onset of the condition, an agent to reduce the frequency or severity of or delay the onset of symptoms of a medical condition in a subject relative to a subject which does not receive the agent.

The term "treating" or "treatment" as used herein denotes reversing, alleviating, inhibiting the progress of, or improving the disorder or condition to which such term applies, or one or more symptoms of such disorder or condition.

The term "fish skin" as used herein refers to an isolated skin tissue derived from a fish. The skin tissue is with or without scales, and preferably without scales. The fish skin according to the invention does not exclude a small amount of flesh linked to the skin tissue.

The fish referred to in this invention is not particularly limited, and can be a marine fish and freshwater fish of *Osteichthyes* and *Chondrichthyes*. Examples of the marine fish are yellowtail fish, bream, coho salmon, cavalla, turbot, *Sebastes* sp., puffer, ray, and tuna. Examples of the freshwater fish are eel, carp, rainbow trout, gold fish, native carp, crucian carp and *Oreochromis* sp. In one preferred embodiment of the invention, the fish includes *Tilapia* and *Oreochromis* of *Sarotherodon* and those of *Cichlidae*; more preferably, the fish is *Oreochromis* sp.

The term "*Aspergillus*" as used herein refers to microorganisms belonging to *Aspergillus* spp., such as *Aspergillus oryzae, Aspergillus niger, Aspergillus phoenicis, Aspergillus sojae, Aspergillus tamarii, Aspergillus flavus, Aspergillus clavatus, Aspergillus fumigatus, Aspergillus terreus* and *Aspergillus nidulans*. Preferably, *Aspergillus* is *Aspergillus oryzae* var. *viridis* BCRC 30133, *Aspergillus oryzae* var. *oryzae* BCRC 30118, *Aspergillus niger* var. *niger* BCRC 32720, *Aspergillus oryzae* var. *oryzae* BCRC 30120 or *Aspergillus phoenicis* BCRC 34164 obtained from FOOD INDUSTRY RESEARCH AND DEVELOPMENT INSTITUTE (NO. 331, SHIHPIN RD., HSINCHU CITY, TAIWAN, R.O.C.).

The Method for Preparing a Fish Skin Fermentation Liquid Obtained by Fermenting Fish Skin with *Aspergillus*

The present invention provides a method for preparing a fish skin fermentation liquid obtained by fermenting fish skin with *Aspergillus*, which method comprises co-culturing the fish skin and *Aspergillus* in a medium.

According to the method of this invention, the fish skin is optionally cut into small pieces, and then added to the medium. The ratio (w/v) of the fish skin and the medium is not specifically restricted, and can be about 1:1 to about 1:100; preferably about 1:5 to about 1:50; more preferably about 1:10 to about 1:20; and most preferably about 1:8. The medium optionally includes a carbon source (such as glucose) and/or nitrogen source (such as peptone). In one preferred embodiment of the invention, the pH of the medium is about 6.5 to 9.5; preferably about 7.0 to 8.0; most preferably about 7.2.

According to the method of this invention, the medium with the fish skin is subjected to a known sterilization procedure (such as under 1.2 Kg/cm$^2$ and 121° C. for 20 minutes or radiation) prior to the addition of microorganism. After cooling, about $1\times10^3$ to about $1\times10^{11}$; preferably about $1\times10^4$ to about $1\times10^{10}$, more preferably about $2\times10^5$ to about $2\times10^9$ *Aspergillus* cells are added to the sterile medium. After inoculation, the medium is cultivated by shaking at about 80 to about 100 rpm at about 20 to about 32° C. for about 5 to about 15 days to obtain the fish skin fermentation liquid obtained by fermenting fish skin with *Aspergillus*. In another embodiment of this invention, the inoculated medium is placed in a fermentation tank and cultivated with air flow rate of about 1 vvm and with stirring speed of about 200 to about 300 rpm at about 25° C. for about 5 to about 15 days to obtain the skin fermentation liquid obtained by fermenting fish skin with *Aspergillus*.

In order to isolate the product, an optional process is performed. First, for example, the solid portion is removed from the fermentation by centrifugation or filtration. If necessary, chromatography, precipitation, ultrafiltration, micro-filtration, nano filtration, reverse osmosis, electrophoresis, electrodialysis or electric focusing is applied for directly isolating the product.

The Composition Comprising the Fish Skin Fermentation Liquid Obtained by Fermenting Fish Skin with *Aspergillus*

The invention also provides a composition which comprises the fish skin fermentation liquid obtained by fermenting fish skin with *Aspergillus* prepared by the method mentioned above. The composition according to the invention can be a food composition, a pharmaceutical composition or a cosmetic composition.

The fish skin fermentation liquid obtained by fermenting fish skin with *Aspergillus* prepared by the method mentioned above can be added to a conventional food composition (i.e. the edible food or drink or precursors thereof) in the manufacturing process of the food composition. Almost all food compositions can be supplemented with the fish skin fermentation liquid obtained by fermenting fish skin with *Aspergillus* of the invention. The food compositions that can be supplemented with the fish skin fermentation liquid obtained by fermenting fish skin with *Aspergillus* of the invention include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The fish skin fermentation liquid obtained by fermenting fish skin with *Aspergillus* of the invention can be formulated with a pharmaceutically or cosmetically acceptable carrier and/or an excipient. As used herein, "carrier" or "excipient" refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The pharmaceutical or cosmetic composition of the invention can be administered topically or systemically by any method known in the art, including, but not limited to intramuscular, intradermal, intravenous, subcutaneous, intraperitoneal, intranasal, oral, mucosal or external routes. In the present invention, depending on the route of administration, the pharmaceutical composition and cosmetic composition can be formulated into various forms, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof.

Utility

The applicants surprisingly found that the fish skin fermentation liquid obtained by fermenting fish skin with *Aspergillus* according to the invention has the ability to inhibit the activity of tyrosinase, inhibit the activity of angiotensin-converting enzyme and/or improve the survival of fibroblasts.

Tyrosinase (EC 1.14.18.1) is a monooxygenase containing copper which is widely distributed in nature. The basic metabolic function of tyrosinase is catalyzing oxidative degradation of tyrosine. In animals, including humans, tyrosinase first converts tyrosine into 3,4-dihydroxyphenyl alanine (DOPA), and then into the corresponding quinone (Dopaquinone), and then into 2-carboxy-2,3-dihydroxy indole 5,6-benzoquinone (Dopachrome), which in turn is converted into more highly oxidative substances by other enzymes, including melanin, which causes pigmentation of the skin. Pharmaceutical experts have accepted the relationship between melanoma and the inhibition of tyrosinase.

Therefore, the fish skin fermentation liquid obtained by fermenting fish skin with *Aspergillus* and the composition thereof according to the invention can be used to treat or prevent excess formation of melanin, spots and freckles after long-term sun exposure, to delay formation of melanin and to lighten the skin.

Angiotensin converting enzyme (ACE) mainly exists in the human vascular endothelial cells, lungs, kidneys and brain. The enzyme converts the inactive angiotensin I into the active angiotensin II by the removal of two amino acids (His-Leu) in the C-terminal, resulting in the vasoconstriction and increase of blood pressure. Artisans skilled in this field know that an ACE inhibitor can be used as a cardiovascular protector for reducing blood pressure and treating myocardial infarction, heart failure, left ventricular dysfunction, stroke and cardiovascular mortality. Therefore, the fish skin fermentation liquid obtained by fermenting fish skin with *Aspergillus* and the composition of the invention have the ability to treat or prevent a cardiovascular disease, such as arterial hypertension (including all types), systolic hypertension, peripheral vascular disease, atherosclerosis, restenosis, heart failure, thrombosis, thromboembolism, angina cordis (stable or unstable), cerebrovascular accident, coronary accident, myocardial infarction, revascularization, and/or complications related to surgery (such as cardiovascular surgery).

The dermis is a three-dimensional connective tissue that mainly comprises dermal fibroblasts, collagen fibers and elastic fibers (elastin), wherein the proteins such as collagen constituting the fibers are generated by the fibroblasts. Therefore, the effect for improving the survival of fibroblasts of the fish skin fermentation liquid obtained by fermenting fish skin with *Aspergillus* and the composition thereof according to the invention can improve skin strength, extension and elasticity and promote wound healing.

The present invention also provides a method for inhibiting the activity of tyrosinase, inhibiting the activity of angiotensin-converting enzyme and/or improving the survival of fibroblasts in a subject in need of such inhibition and/or improvement, which comprises administering to said subject an effective amount of the fish skin fermentation liquid obtained by fermenting fish skin with *Aspergillus* and the composition thereof according to the invention.

The subject in need of the inhibition of the activity of tyrosinase refers to a subject which is recognized and/or diagnosed to need to inhibit the activity of tyrosinase for alleviating and/or treating symptoms caused by the activity of tyrosinase, especially by the overacitivity of tyrosinase. Preferably, the subject refers to a subject afflicted with the excess formation of melanin, spots and freckles after long-term sun exposure.

The subject in need of the inhibition of the activity of angiotensin-converting enzyme refers to a subject which is recognized and/or diagnosed to need to inhibit the activity of angiotensin-converting enzyme for alleviating and/or treating symptoms caused by the activity of angiotensin-converting enzyme, especially by the overactivity of angiotensin-converting enzyme. Preferably, the subject refers to a subject afflicted with a cardiovascular disease, such as arterial hypertension (including all types), systolic hypertension, peripheral vascular disease, atherosclerosis, restenosis, heart failure, thrombosis, thromboembolism, angina cordis (stable or unstable), cerebrovascular accident, coronary accident, myocardial infarction, revascularization, and/or complications related to surgery (such as cardiovascular surgery).

The subject in need of the improvement of the survival of fibroblasts refers to a subject which is recognized and/or diagnosed to need to improve the survival of fibroblasts for alleviating and/or treating symptoms caused by the lack of fibroblasts. Preferably, the subject refers to a subject afflicted poor skin strength, extension and elasticity and wounds.

The present invention also provides a method for inhibiting the activity of angiotensin-converting enzyme in a subject in need of such inhibition comprising administering to said subject an effective amount of a fish skin fermentation composition obtained by co-culturing a fish skin and *Aspergillus* in a medium and collecting the supernatant.

Preferably, the method is for treating a cardiovascular disease in a subject afflicted with the cardiovascular disease.

The following examples are provided to aid those skilled in the art in practicing the present invention.

EXAMPLES

Preparation of a Skin Fermentation Liquid Obtained by Fermenting Fish Skin with *Aspergillus*

(1) Experimental Materials

The fish skin derived from Taiwan tilapia is washed with water and the scales are scraped. The sample is then dried and weighed.

(2) Strain Activation

To freeze-dried tubes containing *Aspergillus oryzae* var. *viridis* BCRC 30133, *Aspergillus oryzae* var. *oryzae* BCRC 30188, *Aspergillus niger* var. *Niger* BCRC 32720, *Aspergillus oryzae* var. *oryzae* BCRC 30120, and *Aspergillus phoenicis* BCRC 34164, respectively, 0.3-0.5 mL of sterile water is added. The bacterial solution is then put into a test tube containing about 5 mL of sterile water, and slightly shaken for dispersion. The 0.1-0.2 mL of cell suspension is plated on a PDA plate, and cultivated at 20-32° C. for 5 to 15 days, and then transferred to a new PDA plate to complete the activation of the bacteria.

(3) Pre-Treatment of the Fermentation Substrate

The segment of fish skin without scales is cut into small pieces. The 6 g (wet weight) of the fish skin and 50 mL of the medium (1% glucose and 0.5% peptone) are put into a 250-mL flask and subjected to sterilization at 121° C. and 1.2 Kg/cm$^2$ for 20 minutes in an autoclave.

(4) Liquid Fermentation

After the bacteria are activated for 7 days, an appropriate amount of sterile water for washing the spores is added to the plate containing them. One mL of the spore solution ($10^{6-10}$ CFU/mL) is inoculated into the sterile medium and mixed. The culture is cultivated at 20-32° C. at a speed of 80-100 rpm in a culture room for 5 to 15 days.

The fermentation liquid is centrifuged at 3000 rpm for 10 minutes and the supernatant is collected. The supernatant is freeze-dried and stored at −18° C. for the subsequent assays. Analysis of the Effect of the Fermentation Liquid Obtained by Fermenting Fish Skin with *Aspergillus*

(1) Assay of the Inhibition of Tyrosinase Activity

The assay described in Choi et al. ("(4-Methoxy-benzylidene) (3-methoxy-phenyl)-amine, a nitrogen analog of stilbene as a potent inhibitor of melanin production;" Chem Pharm Bull.; 2002; 50 (4): 450-452) is modified. The freeze-dried powder of the fermentation liquid obtained by fermenting fish skin with *Aspergillus* obtained as mentioned above and 100 mM borate buffer are prepared to form a sample containing the 100 mg/mL fermentation liquid obtained by fermenting fish skin with *Aspergillus*, and then 40 μL of the sample, 80 μL of phosphate buffer solution (1/15 M, pH 6.8) and 40 μL of 15 mM DOPA (dissolved in 1/15M phosphate buffer solution) are mixed and preheated at 37° C. for 10 minutes. 40 μL (total 30 U) of tyrosinase is mixed and reacted at 37° C. for 20 minutes. The absorbance value of the sample is assayed at a wavelength of 475 nm. The control group is deionized water. The higher value of the absorbance value indicates more production of dopachrome, which represents lower inhibitory activity of tyrosine.

(2) Assay of the Inhibition of Angiotensin-Converting Enzyme Activity

The assay described in Cushman and others ("Spectrophotometric assay and properties of the angiotensin converting enzyme of rabbit lung;" Biochem Pharmacol.; 1971; 20: 1637-1648) is modified. Buffer A (100 mM borate buffer, pH 8.3) and buffer B (containing 600 mM NaCl in 100 mM borate buffer, pH 8.3) are mixed in a 1:1 ratio (pH 8.3) to form AB buffer. The angiotensin I-converting enzyme (1 U) is dissolved in 9.374 mL of AB buffer to form ACE solution (106 mU/mL). The 64.4 mg hippuryl-L-histidyl-L-leucine (HHL) substrate is dissolved in 10 mL of AB buffer to form HHL substrate solution (15 mM).

The 75 μL of the fermentation liquid obtained by fermenting fish skin with *Aspergillus* sample (10 mg/mL) diluted with 100 mM borate buffer solution and 75 μL of ACE solution are mixed in a water bath at 37° C. for 10 minutes with shaking, followed by addition of 75 μL HHL substrate solution. After mixing, the sample is reacted at 37° C. in a water bath for 30 minutes, and the reaction is terminated by adding 250 μL of 1N HCl. The generated hippuric acid is extracted with 750 μL of ethyl acetate. The mixture is centrifuged (3600 rpm, 5 minutes) after shaking for 1 minute. The 500 μL of supernatant is evaporated dried in an 80° C. water bath. The pellet is dissolved in 1 mL of deionized water, and then filtered with a 0.45 μm membrane. 200 μL of the filtrate is added into a 96-well UV plate, and the absorbance values of the filtrate are assayed at the wavelength of 228 nm to obtain the percentage of inhibition of ACE activity. The formula is as follows:

$$\text{Inhibition (\%)} = [(A_C - A_S)/(A_C - A_B)] \times 100\%$$

$A_C$=the absorbance value of the buffer substituted for the fermentation liquid obtained by fermenting fish skin with *Aspergillus*

$A_S$=the absorbance value of the fermentation liquid obtained by fermenting fish skin with *Aspergillus*

$A_B$=the absorbance value of the fermentation liquid obtained by fermenting fish skin with *Aspergillus* to which HCl has been added for termination before the reaction The AB buffer substituted for the fermentation liquid obtained by fermenting fish skin with *Aspergillus* is as a control group. The blank group is 75 μL of the diluted fermentation liquid obtained by fermenting fish skin with *Aspergillus* to which 75 μL of HHL substrate solution has been added; 250 μL of 1N HCl is added to the mixture to terminate the reaction, after which 75 μL of ACE solution is added. The subsequent steps are similar to those of the experimental group.

(3) Assay of the Survival of Fibroblasts (MTT Analysis)

(a) Cell Culture

The assay described in Lee et al. ("Biological activities of the polysaccharides produced from submerged culture of the edible Basidiomycete Grifola frondosa;" Micro Technol.; 2003; 32 (5): 574-581) is modified. The human fibroblast cell line CCD-966SK (obtained by FOOD INDUSTRY RESEARCH AND DEVELOPMENT INSTITUTE (BCRC 60153, ATCC CRL-1881)) is cultured in a medium containing 10% fetal calf serum, 2 mM L-Glutamine acid, 0.1 mM non-essential amino acids and 1.0 mM sodium pyruvate MEM medium at 37° C. and 5% $CO_2$ in an incubator.

(b) MTT Assay

100 μL of the cells are seeded onto a 96-well plate ($2 \times 10^5$ cells/well). After 24 hours, different concentrations of 100 μL of the diluted samples of the fermentation liquid obtained by fermenting fish skin with *Aspergillus* are added to the wells, except for the control group. After 48 hours, the medium is collected. Before assay, 5 g/mL MTT is diluted to 2 mg/Ml with PBS. After removing the medium, the wells are washed with PBS, and then 100 μL of MTT diluent is added into the well. The plate is incubated at 37° C. and 5% $CO_2$ in an incubator for 4 hours, and the MTT diluent is removed. 100 μL of DMSO is added into the wells for dissolving blue formazan crystals. After shaking for 10 minutes, until the crystals are dissolved stably, the absorbance values at wavelength of 570 nm is measured.

(C) Calculation

The serum medium without the fermentation liquid obtained by fermenting fish skin with *Aspergillus* is used as the blank; the survival rate (%)=$(A_S/A_C) \times 100\%$ $A_S$=the absorbance value at 570 nm of the sample with the fermentation liquid obtained by fermenting fish skin with *Aspergillus*

$A_C$=the absorbance value at 570 nm of the sample without the fermentation liquid obtained by fermenting fish skin with *Aspergillus*

(4) Results

The results of the first fermentation liquid obtained by fermenting fish skin with *Aspergillus* sample prepared as mentioned above are shown in Table 1. Before fermentation, the rate of inhibition of tyrosinase activity, the rate of inhibition of ACE activity and the rate of survival of fibroblasts are −21%, 10% and 97%, respectively. After the fermentation with the five *Aspergillus* strains (BCRC 30133, 30118, 32720, 32120, and 34164), the fermentation liquid obtained by fermenting fish skin with *Aspergillus* shows significantly improved inhibition of tyrosinase activity (more than 37 fold relative to the control group), inhibition of ACE activity (more than 5 fold relative to the control group) and survival of fibroblasts (more than 0.9 fold relative to the control group). Compared with the commercially available product Otsu Tai (collagen from the cod skin), inhibition of tyrosinase activity and survival of fibroblasts are the same or better when using the fermentation liquid obtained by fermenting fish skin with *Aspergillus* of the invention.

The results of the second fermentation liquid obtained by fermenting fish skin with *Aspergillus* samples are shown in Table 1. The second fermentation liquid obtained by fermenting fish skin with *Aspergillus* samples are prepared in the same manner as the first fermentation liquid obtained by fermenting fish skin with *Aspergillus* samples except that another batch of fish skin is used. Before fermentation, the rate of inhibition of tyrosinase activity, the rate of inhibition of ACE activity, and the rate of survival of fibroblasts are −21%, 10% and 97%, respectively. After fermentation by the five *Aspergillus* strains (BCRC 30133, 30118, 32720, 32120, and 34164), the fermentation liquid obtained by fermenting fish skin with *Aspergillus* can significantly improve the rate of inhibition of tyrosinase activity (more than 34 fold relative to the control group), the rate of inhibition of ACE activity (more than 6 fold relative to the control group) and the rate of survival of fibroblasts (more than double the control group). Compared with the commercially available product Otsu Tai (collagen from the cod skin), inhibition of tyrosinase activity and survival of fibroblasts are the same or better when using the fermentation liquid obtained by fermenting fish skin with *Aspergillus* of the invention. The results show no significant difference in the effectiveness of different batches of the raw materials. The fermentation liquid obtained by fermenting fish skin with *Aspergillus* can significantly inhibit the activity of tyrosinase, inhibit the activity of angiotensin-converting enzyme and improve the survival of fibroblasts.

TABLE 1

| BCRC No. | Strain | rate of inhibition of tyrosinase activity (%) | fold increase | rate of inhibition of ACE activity (%) | fold increase | rate of survival of fibroblasts (%) | fold increase |
|---|---|---|---|---|---|---|---|
| | Control (before fermentation) | −21 | 1.0 | 10 | 1.0 | 97 | 1.0 |
| 30133 | *Aspergillus oryzae* var. *viridis* | 63 | 85 | 72 | 7.2 | 96 | 0.9 |
| 30118 | *Aspergillus oryzae* var. *viridis* | 18 | 40 | 67 | 6.7 | 125 | 1.3 |
| 32720 | *Aspergillus niger* var. *niger* | 85 | 107 | 61 | 6.1 | 132 | 1.4 |
| 30120 | *Aspergillus oryzae* var. *oryzae* | 15 | 37 | 58 | 5.8 | 109 | 1.1 |
| 34164 | *Aspergillus phoenicis* | 92 | 114 | 63 | 6.3 | 120 | 1.2 |
| | Commercial Otsu Tai | 16 | 38 | 88 | 8.8 | 92 | 0.9 |

TABLE 2

| BCRC No. | Strain | rate of inhibition of tyrosinase activity (%) | fold increase | rate of inhibition of ACE activity (%) | fold increase | rate of survival of fibroblasts (%) | fold increase |
|---|---|---|---|---|---|---|---|
| | Control (before fermentation) | −21 | 1.0 | 10 | 1.0 | 97 | 1.0 |
| 30133 | *Aspergillus oryzae* var. *viridis* | 69 | 91 | 73 | 7.3 | 104 | 1.1 |
| 30118 | *Aspergillus oryzae* var. *viridis* | 24 | 46 | 71 | 7.1 | 127 | 1.3 |
| 32720 | *Aspergillus niger* var. *niger* | 93 | 115 | 64 | 6.4 | 158 | 1.6 |
| 30120 | *Aspergillus oryzae* var. *oryzae* | 12 | 34 | 69 | 6.9 | 117 | 1.2 |
| 34164 | *Aspergillus phoenicis* | 92 | 114 | 64 | 6.4 | 112 | 1.2 |
| | Commercial Otsu Tai | 16 | 38 | 88 | 8.8 | 92 | 0.9 |

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for inhibiting the activity of angiotensin-converting enzyme in a subject in need of such inhibition comprising administering to said subject an effective amount of a fish skin fermentation supernatant,
wherein the fish skin fermentation supernatant is obtained by a process comprising steps of:
providing sterilized fish skin;
co-culturing the sterilized fish skin and *Aspergillus* in a medium to obtain a fermentation liquid; and
centrifuging the fermentation liquid and collecting the fish skin fermentation supernatant,
wherein the fish skin is derived from yellowtail fish, bream, coho salmon, cavalla, turbot, *Sebastes* species, puffer, ray, tuna, eel, carp, rainbow trout, gold fish, native carp, crucian carp and/or *Oreochromis* species, and
wherein *Aspergillus* is selected from the group consisting of *Aspergillus oryzae, Aspergillus niger* and *Aspergillus phoenicis*.

2. The method according to claim 1, wherein the fish skin is derived from *Oreochromis* species.

3. The method according to claim 1, which is for treating a cardiovascular disease in a subject afflicted with the cardiovascular disease.

4. The method according to claim 3, wherein the cardiovascular disease is arterial hypertension, systolic hypertension, peripheral vascular disease, atherosclerosis, restenosis, disease, heart failure, thrombosis, thromboembolism, angina cordis, cerebrovascular accident, coronary accident, myocardial infarction, and/or revascularization.

* * * * *